United States Patent
Fournier

(10) Patent No.: US 8,272,300 B2
(45) Date of Patent: Sep. 25, 2012

(54) HAND TOOL ARTICULATING APPARATUS WITH OFFSET HANDLE

(75) Inventor: Stephen M. Fournier, Bozeman, MT (US)

(73) Assignee: Dr. Slick Company, Belgrade, MT (US)

( * ) Notice: Subject to any disclaimer, the term of this patent is extended or adjusted under 35 U.S.C. 154(b) by 413 days.

(21) Appl. No.: 12/557,005

(22) Filed: Sep. 10, 2009

(65) Prior Publication Data

US 2010/0064862 A1 Mar. 18, 2010

Related U.S. Application Data

(60) Provisional application No. 61/096,474, filed on Sep. 12, 2008.

(51) Int. Cl.
*B25B 7/14* (2006.01)
*A61B 17/00* (2006.01)
(52) U.S. Cl. .......................... 81/313; 606/205
(58) Field of Classification Search .................. 81/313, 81/415, 427.5; 606/205, 208
See application file for complete search history.

(56) References Cited

U.S. PATENT DOCUMENTS

| | | | |
|---|---|---|---|
| 1,664,112 A * | 3/1928 | Junemann | 606/158 |
| 1,913,770 A | 6/1933 | Olenik | |
| 2,082,062 A | 6/1937 | Johnson | |
| 2,789,860 A * | 4/1957 | Knowles | 294/104 |
| 2,863,459 A * | 12/1958 | Casper | 606/147 |
| 2,962,024 A * | 11/1960 | Raymond | 606/208 |
| 3,083,711 A | 4/1963 | Ramsay | |
| 3,101,715 A | 8/1963 | Glassman | |
| 3,349,772 A | 10/1967 | Rygg | |
| D229,724 S | 12/1973 | Ericson et al. | |
| 3,823,719 A * | 7/1974 | Cummings | 606/208 |
| 4,140,124 A * | 2/1979 | Curutchet | 606/174 |
| 4,559,944 A * | 12/1985 | Jaeger | 604/98.01 |
| 4,596,249 A | 6/1986 | Freda et al. | |
| 4,635,510 A | 1/1987 | Box | |
| 4,662,372 A | 5/1987 | Sharkany et al. | |

(Continued)

FOREIGN PATENT DOCUMENTS

EP 1656893 A2 5/2006

OTHER PUBLICATIONS

PCT/US/09/056589, Apr. 2010, Written Opinion.

(Continued)

*Primary Examiner* — David B Thomas
(74) *Attorney, Agent, or Firm* — Wells St. John, P.S.

(57) ABSTRACT

A hand tool articulating apparatus has a pair of elongate members coupled for articulation about a pivot axis. Each elongate member has a clamping jaw on one side of the pivot axis and an arm extending to a handle on the other side of the pivot axis. One of the arms extends from the pivot axis along a first axis over a first distance to a first loop extending outwardly from the first axis and away from the other of the arms. The other of the arms has a first portion and a second portion. The first portion extends along a second axis from the pivot axis a shorter distance than the one arm. The second portion extends inclined to the second axis along a third axis away from the one arm to a second loop. The second loop extends outwardly from the third axis away from the pivot axis.

21 Claims, 2 Drawing Sheets

U.S. PATENT DOCUMENTS

| | | | |
|---|---|---|---|
| 4,934,222 A * | 6/1990 | Rittmann et al. | 81/427.5 |
| D326,911 S | 6/1992 | Epstein | |
| D327,124 S | 6/1992 | Heaton | |
| 5,395,364 A * | 3/1995 | Anderhub et al. | 606/51 |
| D365,878 S | 1/1996 | Blake | |
| D366,699 S | 1/1996 | Blake | |
| D366,700 S | 1/1996 | Blake | |
| 5,624,454 A | 4/1997 | Palti et al. | |
| 5,697,942 A | 12/1997 | Palti | |
| D390,954 S | 2/1998 | Kumar et al. | |
| D391,818 S | 3/1998 | Carlson | |
| 6,081,952 A * | 7/2000 | Haxton | 7/107 |
| 6,673,009 B1 | 1/2004 | Vanden Hoek et al. | |
| 6,682,548 B2 * | 1/2004 | Lang et al. | 606/205 |
| 6,761,725 B1 | 7/2004 | Grayzel et al. | |
| 6,834,571 B1 * | 12/2004 | Lowe et al. | 81/427.5 |
| 7,087,070 B2 * | 8/2006 | Flipo | 606/205 |
| D536,587 S | 2/2007 | Zaremski | |
| D536,941 S | 2/2007 | Nenadich et al. | |
| D537,312 S | 2/2007 | Nenadich et al. | |
| D538,612 S | 3/2007 | Nenadich et al. | |
| D543,662 S | 5/2007 | Bivona et al. | |
| D544,148 S | 6/2007 | Bivona et al. | |
| 7,438,717 B2 * | 10/2008 | Tylke | 606/108 |
| 7,677,142 B1 * | 3/2010 | Cousin | 81/427.5 |
| 7,846,177 B2 * | 12/2010 | Carpenter et al. | 606/205 |
| 2003/0144693 A1 * | 7/2003 | Flipo | 606/205 |
| 2004/0220601 A1 * | 11/2004 | Lang et al. | 606/167 |
| 2006/0079931 A1 * | 4/2006 | Brennan et al. | 606/205 |
| 2006/0260135 A1 | 11/2006 | Khan-Sullman | |
| 2008/0172886 A1 | 7/2008 | Jun | |
| 2009/0056509 A1 * | 3/2009 | Anderson | 81/342 |

OTHER PUBLICATIONS

PCT/US/09/056589, Apr. 2010, Search Report.
W. Lorenz; Tungsten Carbide Instruments Needle Holders with Pow'R Grip.

* cited by examiner

HAND TOOL ARTICULATING APPARATUS WITH OFFSET HANDLE

CROSS-REFERENCE TO RELATED APPLICATION

This application claims the benefit of U.S. Provisional Application Ser. No. 61/096,474, filed Sep. 12, 2008, which is incorporated herein by reference in its entirety.

BACKGROUND OF THE INVENTION

1. Technical Field

This invention relates generally to clamps, and more particularly clamps used to squeeze, cut, clamp, grip, crush, or squeeze, such as pliers, scissors, forceps, nut crackers, for example, used in fields of fishing, mechanics, and the medical field, for example.

2. Related Art

Clamps are commonly used to grip objects to facilitate manipulating the object being gripped. For example, forceps are commonly used in fishing, particularly in fly fishing, wherein very fine fishing line often needs to be gripped. In addition, the forceps are commonly used to crush barbs on hooks, for removing hooks from fish, and for tying knots. It is also common practice to use forceps in medical procedures, such as in surgery, to grasp other instruments, suture and vessels.

Clamps have a pair of elongate members pivotally attached to one another. The elongate members typically have three main components: jaws, arms and handles. The arms and handles are on one side of an articulation or pivot axis, and the jaws are on the other side of the pivot axis. The jaws commonly have smooth, striated, cross hatched, roughened, serrated or scored surfaces to enhance their gripping ability. The arms are typically symmetrical and extend in mirrored relation to one another. The handles are also typically symmetrical and configured in mirrored relation to one another, such as shown in FIG. 1 of the prior art. Although these clamps are useful, they can prove awkward or cumbersome in use, given their unnatural configuration. In additional, the desired gripping strength can be difficult to attain due to the user's hands being positioned unnaturally while applying a clamping force via the symmetrically oriented handles.

SUMMARY OF THE INVENTION

An articulating apparatus has a pair of elongate members coupled for articulation about a pivot axis. Each elongate member has a clamping jaw on one side of the pivot axis and an arm extending to a handle on the other side of the pivot axis. One of the arms extends from the pivot axis along a first axis over a first distance to a first loop extending outwardly from the first axis and away from the other of the arms. The other of the arms has a first portion and a second portion. The first portion extends along a second axis from the pivot axis a shorter distance than the one arm. The second portion extends inclined to the second axis along a third axis away from the one arm to a second loop. The second loop extends outwardly from the third axis away from the pivot axis. As such, the first and second loops are configured for ergonomic use and provide an ability to maximize a clamping force applied by the clamping jaws.

According to another aspect of the invention, a locking member extends from a portion of the second loop toward the second axis and is configured for locking engagement with another locking member extending from adjacent the first loop. Accordingly, the locking members can be precisely interlocked via tactile feedback through the first and second loops.

BRIEF DESCRIPTION OF THE DRAWINGS

These and other aspects, features and advantages of the invention will become more readily apparent when considered in connection with the following detailed description of presently preferred embodiments and best mode, appended claims and accompanying drawings, in which:

DETAILED DESCRIPTION OF A PRESENTLY PREFERRED EMBODIMENT

Figure 2:
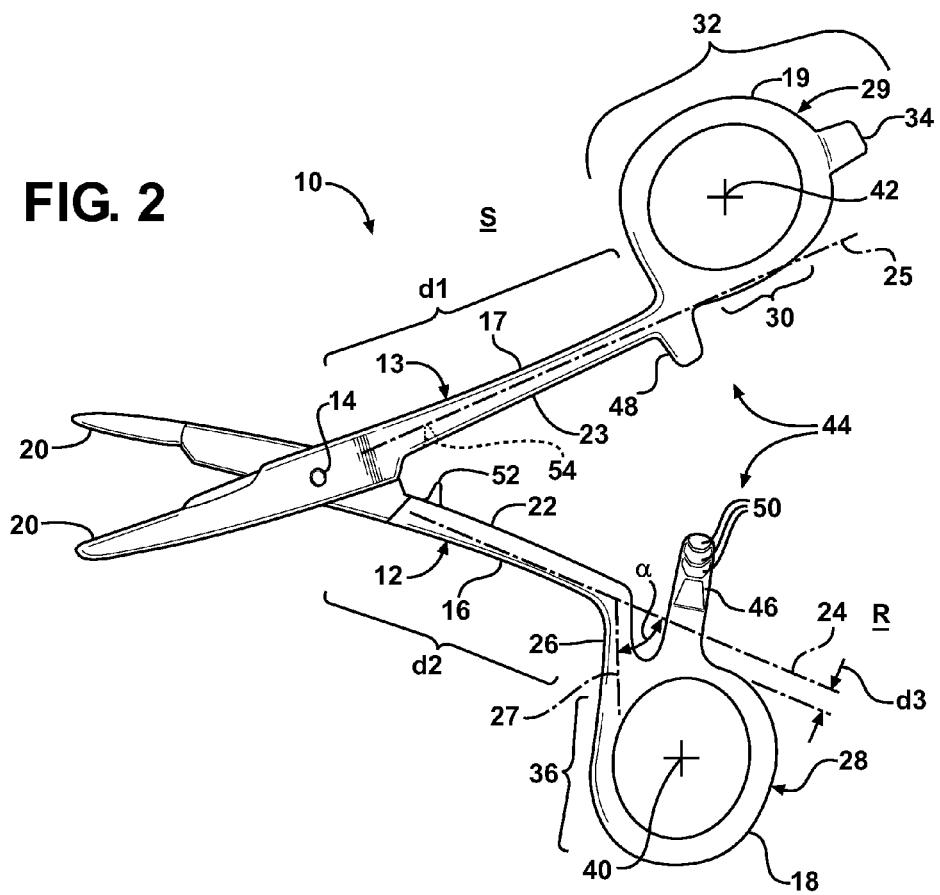
FIG. 2 is a plan view of an articulating clamp constructed according to one presently preferred aspect of the invention shown in an open, unclamped position.
Figure 3:
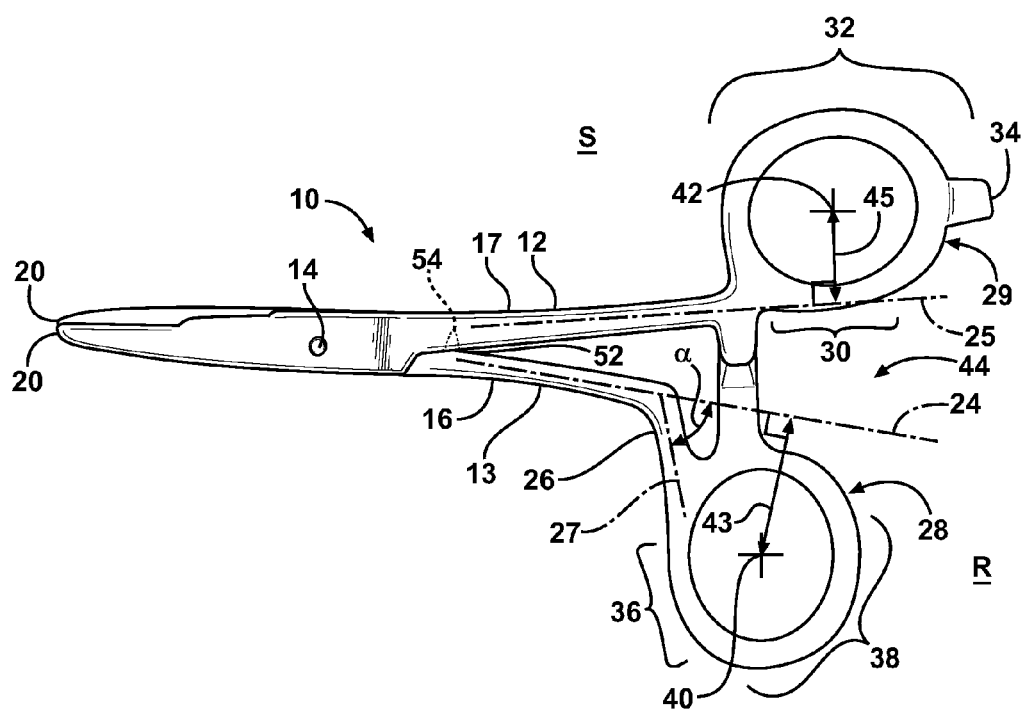
FIG. 3 is a plan view of the articulating clamp of FIG. 2 shown in a closed, clamped position.

Referring in more detail to the drawings, FIGS. 2 and 3 illustrate an articulating apparatus 10, represented here, by way of example and without limitation, as a clamp constructed in accordance with one aspect of the invention for gripping objects, such as fishing hooks, fishing line, sutures, or blood vessels, such as in a surgical procedure, by way of example and without limitation. The articulating apparatus 10 can take other constructions in accordance with the invention, such as scissors, pliers and other assorted hand operated tools for use in fishing, medical and hobby industries, for example. Hereafter, the articulating apparatus in referred to as "clamp" for sake of conciseness. The clamp 10 has a pair of elongate members 12, 13 coupled to one another for articulated, pivoting movement relative to one another about a pivot axis 14. The elongate members 12, 13 each have a respective arm portion, referred to hereafter as arms 16, 17 and a respective handle portion, referred to hereafter as handles 18, 19, on one side of the pivot axis 14 and a clamp member or jaw 20 on the other side of the pivot axis 14. One of the handles, and represented here as the handle 18, is offset relative to the other handle 19, thereby providing an improved ergonomic gripping configuration for gripping by a thumb and middle finger and providing a user with an ability to more readily and precisely exert an increased clamping force between the jaws 20.

The arms 16, 17 each have a straight or substantially straight, linear portion 22, 23, respectively, extending away from the pivot axis 14 a predetermined distance along respective first and second axes 24, 25. One of the arms 17 has a straight, linear portion 23 that extends over a first distance d1 along a first axis 25, while the other arm 16 has a straight, linear first portion 22 that extends over a second distance d2 along a second axis 24, wherein the second distance d2 is shorter than the first distance d1. Accordingly, the straight, linear portions 22, 23 are unequal in length. The arm 16, thus, extends over a shorter straight, linear distance than the other arm 17.

The arm 16 has a straight, linear leg portion, also referred to as second portion 26, that extends from the straight, linear first portion 22 at an inclination outwardly from the axis 24 and away from the other arm 17. As such, the second portion 26 provides the arm 16 with a generally L-shaped configuration. The second portion 26 is represented here as being inclined and extending along a third axis 27 that is generally perpendicular to the first axis 24, with generally perpendicular being an angle a between about 75-90 degrees. The length of the second portion 26 is such that the overall length of the arm 16, including both the first portion 22 and the second portion 26, is the same or substantially the same as the arm 17. Accordingly, if the second portion 26 were bent to be coaxial with the first portion 22, the arms 16, 17 would extend the same or substantially the same distance from the pivot axis 14.

The handles 18, 19 are attached to the respective arms 16, 17 and can be provided as continuous circumferential loops 28, 29, respectively, to allow the thumb and selected finger, typically a middle finger, to be fully encircled, and thus, captured upon being inserted within the loops of the respective handles. As such, the arms 16, 17 and jaws 20 can be readily manipulated and clamped toward one another and then moved away from one another by respective movement of the thumb and finger toward and away from one another. The loops 28, 29 are represented here as being generally circular or oval, however other geometries could be used.

The loop 29, also referred to as the first loop, is attached to the end of the arm 17 such that an arc or relatively small segment 30 of the loop 29 is substantially tangent or collinear with the axis 25. A remaining arc portion or relatively large segment 32 of the first loop 29 extends laterally outwardly and away from the first axis 25, and also away from the second axis 24. As such, the large segment 32 faces generally laterally toward an outer side S of the clamp 10. The loop 29 is represented here, by way of example and without limitation, as having an accessory tool 34 extending radially outwardly therefrom. The accessory tool 34 is provided here as a tapered, flat screwdriver, although it could be configured differently, as desired.

The loop 28, also referred to as the second loop, is attached to the end of the arm 16, and more particularly to the end of the second portion 26 of the arm 16, such that an arc or relatively small segment 36 of the second loop 28 is substantially tangent or collinear with the third axis 27 of the second portion 26. A remaining arc portion or relatively large segment 38 (FIG. 3) of the loop 28 extends rearwardly from the third axis 27 and away from the pivot axis 14. As such, the large segment 38 faces generally rearwardly toward a rear end R of the clamp 10 such that the entire second loop 28 is spaced a distance d3 from the second axis 24. Accordingly, the loops 28, 29 extend away from their respective axes 27, 25 such that if the second portion 26 were straightened in coaxial relation with first portion 22, the loops 28, 29 would substantially overlie one another.

Figure 1:
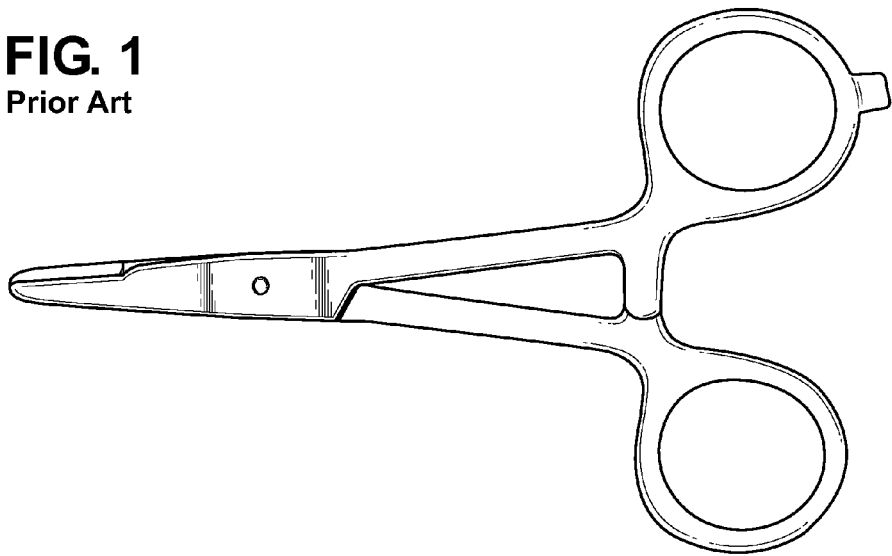
FIG. 1 is a plan view of an articulating clamp constructed according to prior art shown in a closed position.

Each of the loops 28, 29 has a geometric center 40, 42, respectively. The geometric center 40 of the loop 28 is located a first distance 43 perpendicular to the axis 24 and the geometric center 42 is located a second distance 45 perpendicular to the axis 25, wherein the first distance 43 is greater than the second distance 45. The increased distance between the geometric center 40 and the axis 24, given the loops 28, 29 are substantially the same size, provides an increased lever arm, which provides an ability to apply an increased clamping force between the jaws 20. This ability to apply an increased clamping force is due at least in part to the leg portion 26 extending the geometric center outwardly from the axis 24, unlike the prior art of FIG. 1, wherein there is no such leg portion. Further, the geometric center 40 of the loop 28 is located forward of the geometric center 42 of the loop 29, thereby providing a more ergonomic configuration of the loops 28, 29 than the prior art of FIG. 1. The middle finger is able to remain in a more natural position with the loop 28 being slightly forward of the loop 29. This results from the arm 16 being shorter than the arm 17.

A locking device 44 is provided for locking the arms 16, 17 together such that clamping faces of the jaws 20 contact each other in an abutting, locked manner. The locking device 44 includes two locking members, also referred to as tabs 46, 48, with one tab 46 extending directly from a bottom portion of the loop 28 toward and across the second axis 24 and the other tab 48 extending from adjacent the loop 29. Each of the tabs 46, 48 has a plurality of notches 50, with the notches 50 of one tab 46 being configured to releasably interlock with the notches 50 of the other tab 48. With the tab 46 extending from the loop 28 and the other tab 48 extending from the arm 17 immediately adjacent the loop 29, the user is able to the tactile feedback required to precisely lock the jaws 20 as needed to apply the desired clamping force between the jaws 20.

Further, to facilitate maintaining the arms 16, 17 in their proper aligned orientation with one another while being clamped together, one arm 16 has a tapered guide pin 52 extending outwardly therefrom and the other arm 17 has a receptacle 54 sized for close receipt of the guide pin 52. As such, as the arms 16, 17 are being articulated toward one another, the tapered guide pin 52 enters the receptacle 54, thereby preventing the arms 16, 17 from shifting laterally relative to one another. Accordingly, as the arms 16, 17 are being moved toward their clamped position, the jaws 20 are assured of being clamped in proper orientation against one another.

Obviously, many modifications and variations of the present invention are possible in light of the above teachings. It is, therefore, to be understood that within the scope of the appended claims, the invention may be practiced otherwise than as specifically described.

What is claimed is:

1. A hand tool articulating apparatus, comprising:
a pair of elongate members coupled for articulation about a pivot axis, said elongate members each having a clamping jaw on one side of said pivot axis and an arm extending to a handle on the other side of said pivot axis, one of said arms extending from said pivot axis along a first axis over a first distance to a first loop extending outwardly from said first axis and away from the other of said arms, the other of said arms having a first portion and a second portion, said first portion extending along a second axis from said pivot axis a shorter distance than said one arm, said second portion being inclined to said second axis and extending along a third axis away from said one arm to a second loop.

2. The hand tool articulating apparatus of claim 1 wherein said first loop has a portion substantially tangent to said first axis.

3. The hand tool articulating apparatus of claim 2 wherein said second loop has a portion substantially tangent to said third axis.

4. The hand tool articulating apparatus of claim 3 wherein said second loop has a geometric center located a first distance perpendicular to said second axis and said first loop has a geometric center located a second distance perpendicular to said first axis, said first distance being greater than the second distance.

5. The hand tool articulating apparatus of claim 4 wherein said geometric center of said second loop is forward of said geometric center of said first loop.

6. The hand tool articulating apparatus of claim 3 wherein said second loop is entirely spaced from said second axis.

7. The hand tool articulating apparatus of claim 1 wherein a locking member extends directly from a portion of said second loop toward said second axis and another locking member extends from said one arm, said locking members being configured for locking engagement with one another.

8. The hand tool articulating apparatus of claim 1 wherein said arms extend substantially the same distance from said pivot axis when said first and second portions are straightened in collinear relation with one another.

9. The hand tool articulating apparatus of claim 1 wherein said loops substantially overlie one another when said first and second portions are straightened in collinear relation with one another.

10. The hand tool articulating apparatus of claim 1 wherein said second loop extends outwardly from said third axis away from said pivot axis.

11. A clamp apparatus comprising:
   a plurality of elongate members which are coupled with one another at a pivot and wherein at least one of the elongate members is configured to rotate about the pivot;
   wherein the elongate members individually include a clamp member which extends outwardly from the pivot in a first direction, an arm portion which extends outwardly from the pivot in a second direction which is substantially opposite to the first direction, and a handle which is connected with the arm portion;
   wherein the arm portions extend away from the pivot along respective axes and a geometric center of the handle of one of the elongate members is spaced a perpendicular distance from the axis of the respective arm portion of the one elongate member which is greater than a perpendicular distance between a geometric center of the handle of an other of the elongate members and the axis of the respective arm portion of the other elongate member; and
   wherein each of the handles is positioned outside of the axis of its respective arm portion away from the other of the handles.

12. The apparatus of claim 11 wherein the arm portion of the one elongate member includes a first portion which extends along the respective axis of the arm portion of the one elongate member and a second portion which extends outwardly away from the other elongate member and the respective axis of the first portion, and wherein the handle of the one elongate member is connected with the second portion.

13. The apparatus of claim 12 wherein the second portion extends along an axial direction which is generally perpendicular to the axis of the first portion.

14. The apparatus of claim 12 wherein a length of the first portion is less than a length of the arm portion of the other elongate member which extends along the respective axis of the arm portion of the other elongate member.

15. The apparatus of claim 12 wherein the handle of the one elongate member extends outwardly from the second portion away from the pivot, and wherein the handle of the other elongate member extends outwardly from the arm portion of the other elongate member away from the one elongate member.

16. The apparatus of claim 11 wherein the geometric center of the handle of the one elongate member is spaced closer to the pivot than the geometric center of the handle of the other elongate member.

17. The apparatus of claim 16 wherein the arm portions extend away from the pivot along respective axes, wherein the arm portion of the one of the elongate members includes a first portion which extends along the respective axis of the arm portion of the one of the elongate members and a second portion which extends outwardly away from the other of the elongate members and the respective axis of the first portion, and wherein the handle of the one of the elongate members is connected with the second portion.

18. The apparatus of claim 17 wherein the second portion extends along an axial direction which is generally perpendicular to the axis of the first portion.

19. The apparatus of claim 17 wherein a length of the first portion is less than a length of the arm portion of the other of the elongate members which extends along the respective axis of the arm portion of the other of the elongate members.

20. The apparatus of claim 17 wherein the handle of the one of the elongate members extends outwardly from the second portion away from the pivot, and wherein the handle of the other of the elongate members extends outwardly from the arm portion of the other of the elongate members away from the one of the elongate members.

21. A clamp apparatus comprising:
   a plurality of elongate members which are coupled with one another at a pivot and wherein at least one of the elongate members is configured to rotate about the pivot;
   wherein the elongate members individually include a clamp member which extends outwardly from the pivot along a respective axis in a first direction, an arm portion which extends outwardly from the pivot in a second direction which is substantially opposite to the first direction, and a handle which is connected with the arm portion;
   wherein the arm portions individually include interior and exterior sides at the pivot wherein the interior side of one of the arm portions is closer to the other of the arm portions compared with the exterior side of the one of the arm portions;
   wherein the handles of the elongate members are offset with respect to one another wherein a geometric center of the handle of one of the elongate members is closer to the pivot compared with a geometric center of the handle of an other of the elongate members;
   wherein the handle of the one of the elongate members extends outward from the interior side of the arm portion of the one of the elongate members and the handle of the other of the elongate members extends outward from the exterior side of the arm portion of the other of the elongate members; and
   wherein substantially the entireties of the clamp members extend away from the pivot along their respective axes.

\* \* \* \* \*